United States Patent
Chen et al.

(10) Patent No.: US 9,415,125 B2
(45) Date of Patent: Aug. 16, 2016

(54) WIRELESS, REUSABLE, RECHARGEABLE MEDICAL SENSORS AND SYSTEM FOR RECHARGING AND DISINFECTING THE SAME

(71) Applicant: Covidien LP, Mansfield, MA (US)

(72) Inventors: Bo Chen, Louisville, CO (US); Friso Schlottau, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 328 days.

(21) Appl. No.: 14/070,126

(22) Filed: Nov. 1, 2013

(65) Prior Publication Data

US 2014/0056757 A1     Feb. 27, 2014

Related U.S. Application Data

(63) Continuation of application No. 13/462,291, filed on May 2, 2012, now abandoned.

(51) Int. Cl.
| | |
|---|---|
| *A61L 2/16* | (2006.01) |
| *A61L 2/10* | (2006.01) |
| *A61L 2/18* | (2006.01) |
| *A61L 2/20* | (2006.01) |

(Continued)

(52) U.S. Cl.
CPC .............. *A61L 2/10* (2013.01); *A61B 5/14551* (2013.01); *A61L 2/16* (2013.01); *A61L 2/18* (2013.01); *A61L 2/20* (2013.01); *A61L 2/24* (2013.01); *A61B 5/002* (2013.01); *A61B 5/6803* (2013.01); *A61B 5/6816* (2013.01); *A61B 5/6826* (2013.01); *A61B 2560/028* (2013.01); *A61B 2560/0214* (2013.01); *A61L 2202/14* (2013.01); *A61L 2202/24* (2013.01); *H02J 7/022* (2013.01)

(58) Field of Classification Search
CPC ............... A61L 2/10; A61L 2/16; A61L 2/18; A61L 2/20; A61L 2/24
USPC ......................................................... 422/28
See application file for complete search history.

(56) References Cited

U.S. PATENT DOCUMENTS

| | | | |
|---|---|---|---|
| 4,421,298 A | 12/1983 | Kujawski | |
| 4,427,298 A * | 1/1984 | Fahy | ................... B01F 15/0429 137/624.18 |

(Continued)

FOREIGN PATENT DOCUMENTS

| | | |
|---|---|---|
| EP | 702931 | 3/1996 |
| EP | 1945099 | 7/2008 |

(Continued)

OTHER PUBLICATIONS

"Smaller Product, Tighter Tolerances Pose Dispensing Challenges for Medical Device Manufacturer", Adhesive Age, Oct. 1997, 40-41.

(Continued)

*Primary Examiner* — Sean E Conley
*Assistant Examiner* — Donals Spamer
(74) *Attorney, Agent, or Firm* — Fletcher Yoder PC

(57) ABSTRACT

Embodiments described herein may include systems and method for monitoring physiological parameters of a patient. Specifically, embodiments disclose wireless, reusable, rechargeable medical sensors that include an inductive coil coupled to a rechargeable battery. Additionally, embodiments disclose systems and methods for recharging and disinfecting the disclosed medical sensors.

21 Claims, 13 Drawing Sheets

(51) Int. Cl.
*A61L 2/24* (2006.01)
*A61B 5/1455* (2006.01)
*H02J 7/02* (2016.01)
*A61B 5/00* (2006.01)

(56) References Cited

U.S. PATENT DOCUMENTS

| | | | |
|---|---|---|---|
| 5,170,786 | A | 12/1992 | Thomas et al. |
| 5,425,360 | A | 6/1995 | Nelson |
| 5,671,529 | A | 9/1997 | Nelson |
| 5,776,059 | A | 7/1998 | Kaestle et al. |
| 6,072,299 | A | 6/2000 | Kurle et al. |
| 6,592,816 | B1 * | 7/2003 | Ebel .......... A61L 2/10 250/455.11 |
| 6,618,602 | B2 | 9/2003 | Levin |
| 6,678,543 | B2 | 1/2004 | Diab et al. |
| 6,961,600 | B2 | 11/2005 | Kohl et al. |
| 7,052,469 | B2 | 5/2006 | Minamiura et al. |
| 7,161,484 | B2 | 1/2007 | Tsoukalis |
| 7,277,752 | B2 | 10/2007 | Matos |
| 7,382,247 | B2 | 6/2008 | Welch et al. |
| 7,387,607 | B2 | 6/2008 | Holt et al. |
| 2003/0106930 | A1 | 6/2003 | Williams |
| 2004/0182855 | A1 * | 9/2004 | Centanni .......... A61L 2/07 219/628 |
| 2005/0017864 | A1 | 1/2005 | Tsoukalis |
| 2005/0075550 | A1 | 4/2005 | Lindekugel |
| 2005/0119586 | A1 | 6/2005 | Coyle et al. |
| 2006/0069319 | A1 | 3/2006 | Elhag et al. |
| 2006/0079794 | A1 | 4/2006 | Liu et al. |
| 2006/0253010 | A1 | 11/2006 | Brady et al. |
| 2006/0276714 | A1 | 12/2006 | Holt et al. |
| 2006/0282001 | A1 | 12/2006 | Noel et al. |
| 2007/0032707 | A1 | 2/2007 | Coakley et al. |
| 2007/0032708 | A1 | 2/2007 | Eghbal et al. |
| 2007/0032709 | A1 | 2/2007 | Coakley et al. |
| 2007/0032710 | A1 | 2/2007 | Rariden et al. |
| 2007/0032711 | A1 | 2/2007 | Coakley et al. |
| 2007/0032712 | A1 | 2/2007 | Rariden et al. |
| 2007/0032713 | A1 | 2/2007 | Eghbal et al. |
| 2007/0032715 | A1 | 2/2007 | Eghbal et al. |
| 2007/0032716 | A1 | 2/2007 | Rariden et al. |
| 2007/0078309 | A1 | 4/2007 | Matlock |
| 2007/0078315 | A1 | 4/2007 | Kling et al. |
| 2007/0078317 | A1 | 4/2007 | Matlock |
| 2007/0100218 | A1 | 5/2007 | Sweltzer et al. |
| 2007/0100219 | A1 | 5/2007 | Sweltzer et al. |
| 2007/0106132 | A1 | 5/2007 | Elhag et al. |
| 2007/0112260 | A1 | 5/2007 | Diab et al. |
| 2007/0179386 | A1 | 8/2007 | Michard et al. |
| 2007/0185385 | A1 | 8/2007 | Noguchi et al. |
| 2007/0267475 | A1 | 11/2007 | Hoglund et al. |
| 2007/0293820 | A1 | 12/2007 | Dacquay et al. |
| 2008/0018454 | A1 | 1/2008 | Chan et al. |
| 2008/0082018 | A1 | 4/2008 | Sackner et al. |
| 2008/0091089 | A1 | 4/2008 | Guillory et al. |
| 2008/0091090 | A1 | 4/2008 | Guillory et al. |
| 2008/0094228 | A1 | 4/2008 | Welch et al. |
| 2008/0146890 | A1 | 6/2008 | Leboeuf et al. |
| 2008/0195166 | A1 | 8/2008 | Sun et al. |
| 2008/0287758 | A1 | 11/2008 | Benaron et al. |
| 2009/0038648 | A1 | 2/2009 | Langford |
| 2009/0240125 | A1 | 9/2009 | Such et al. |
| 2010/0078046 | A1 | 4/2010 | Labib et al. |
| 2010/0189598 | A1 | 7/2010 | Fraundorfer |
| 2010/0201311 | A1 | 8/2010 | Lyell Kirby |
| 2010/0249552 | A1 | 9/2010 | Price |
| 2011/0057609 | A1 | 3/2011 | Smith et al. |
| 2011/0074342 | A1 | 3/2011 | MacLaughlin |
| 2011/0076192 | A1 | 3/2011 | Robitaille et al. |
| 2011/0213216 | A1 | 9/2011 | McKenna et al. |
| 2012/0116380 | A1 | 5/2012 | Madan et al. |

FOREIGN PATENT DOCUMENTS

| | | |
|---|---|---|
| EP | 1986543 | 11/2008 |
| WO | 2004084720 | 10/2004 |
| WO | 2006079862 | 8/2006 |
| WO | 2007131064 | 11/2007 |
| WO | 2007131066 | 11/2007 |
| WO | 2007141121 | 12/2007 |
| WO | 2008076464 | 6/2008 |

OTHER PUBLICATIONS

Sokwoo, Rhee et al., "The Ring Sensor: a New Ambulatory Wearable Sensor for Twenty-Four Hour Patient Monitoring", Proceedings of the 20th Annual International Conference of the IEEE Engineering in Medicine and Biology Society, 1998, vol. 20, No. 4, Cambridge, MA.
Yang, Boo-Ho et al., "A Twenty-Four Hour Tele-Nursing System Using a Ring Sensor", Proceedings of the 1998 IEEE International Conference on Robotics & Automation, May 1998, Leuven, Belgium.
Yang, Boo-Ho et al., "Development of the ring sensor for the healthcare automation", Robotics and Autonomous Systems, May 21, 1999, 273-281, Cambridge, MA.
Rhee, Sokwoo et al., "Artifact-Resistant, Power-Efficient Design of Finger-Ring Plethsmographic Sensors Part I: Design and Analysis", Proceedings of the 22nd Annual EMBS International Conference, Jul. 23-28, 2000, Chicago, IL.
Rhee, Sokwoo et al., "Artifact-Resistant, Power-Efficient Design of Finger-Ring Plethsmographic Sensors Part II: Prototyping and Benchmarking", Proceedings of the 22nd Annual EMBS International Conference, Jul. 23-28, 2000, Chicago, IL.
Gisiger, P.A. et al., "OxiCarbo, a single sensor for the non-invasive measurement of arterial oxygen saturation and CO2 partial pressure at the ear lobe", Sensors and Actuators B, 2001, Basel, Switzerland.
Rhee, Sokwoo et al., "Artifact-Resistant Power-Efficient Design of Finger-Ring Plethsmographic Sensors", IEEE Transactions on Biomedical Engineering, Jul. 2001, vol. 48, No. 7, Cambridge MA.
Schultz, Christian Eric, "Design of a Pulse Oximetry Sensor Housing Assembly", May 2000, California State University, Long Beach.
International Search Report and Written Opinion for PCT Application No. PCT/US2013/037702 dated Aug. 29, 2013; 7 pgs.

* cited by examiner

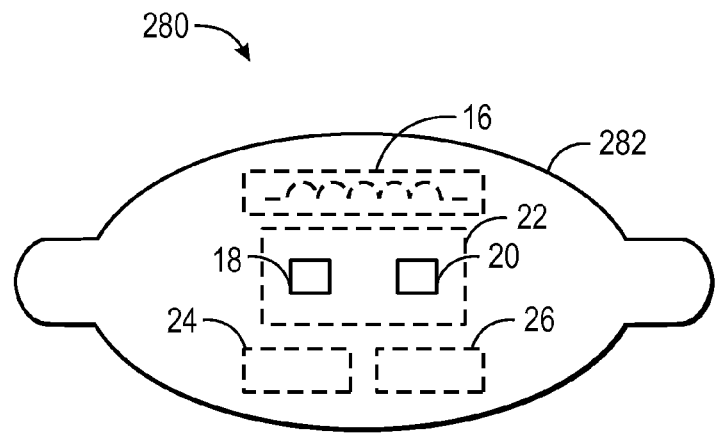
FIG. 11
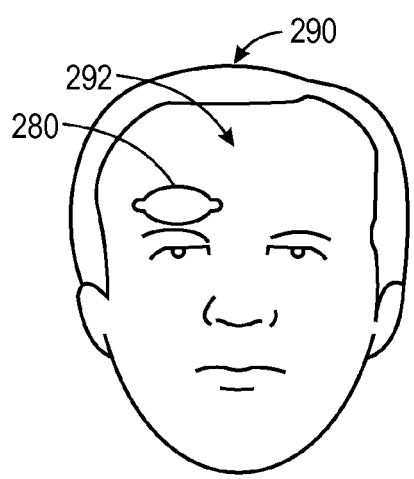 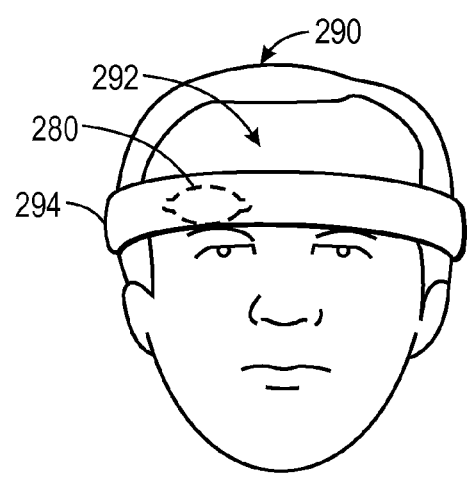
FIG. 12A          FIG. 12B

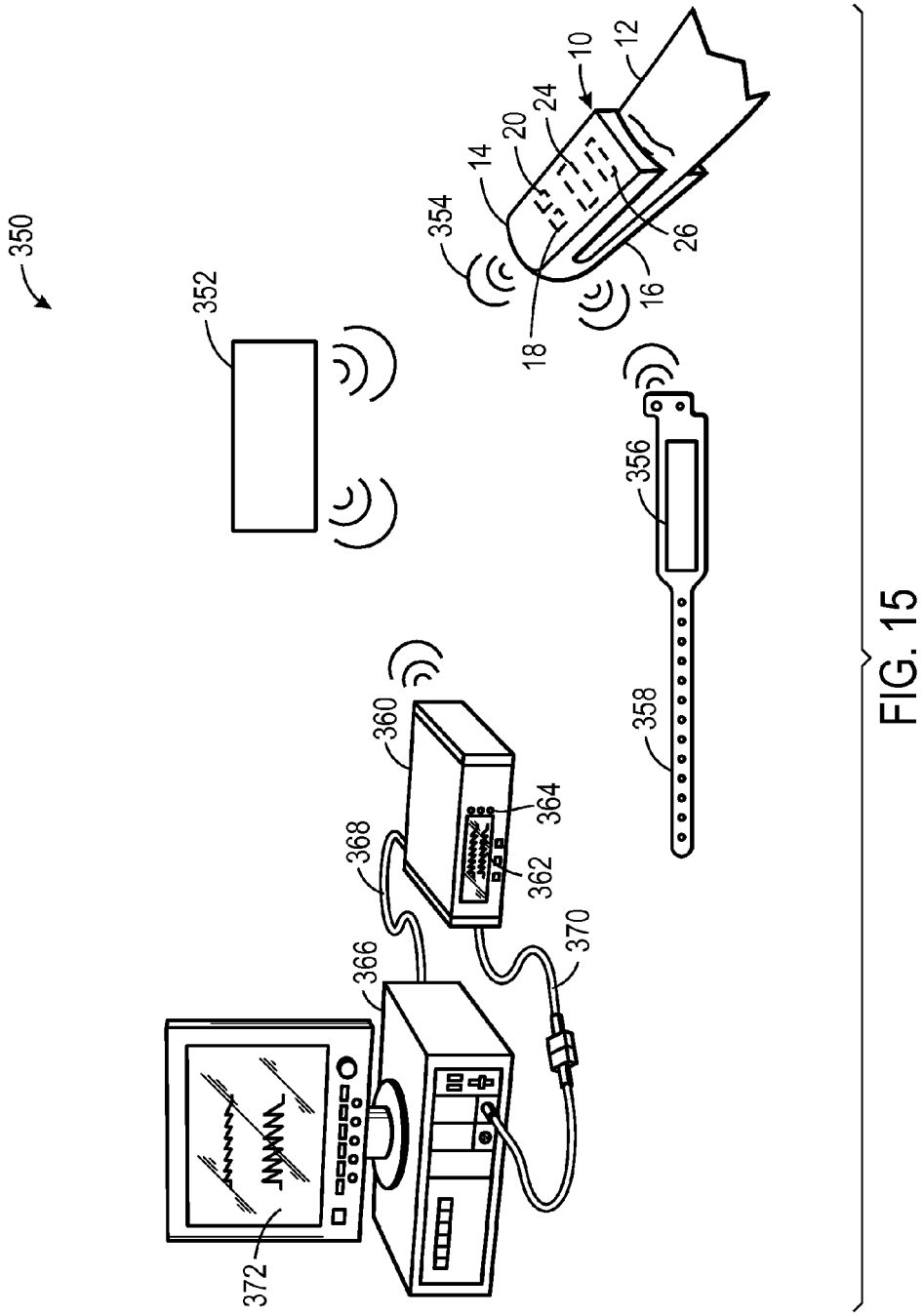

WIRELESS, REUSABLE, RECHARGEABLE MEDICAL SENSORS AND SYSTEM FOR RECHARGING AND DISINFECTING THE SAME

CROSS-REFERENCE TO RELATED APPLICATIONS

This application is a continuation of U.S. patent application Ser. No. 13/462,291, entitled "Wireless, Reusable, Rechargeable Medical Sensors and System for Recharging and Disinfecting the Same," filed May 2, 2012, which is herein incorporated by reference in its entirety.

BACKGROUND

The present disclosure relates generally to medical devices and, more particularly, to wireless medical sensors such as those used for pulse oximetry.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. These devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters and other types of monitoring devices may use either disposable sensors, which are discarded after a single use, or reusable sensors. These reusable sensors may lower the overall cost of the sensor per use, however the sensors must be thoroughly disinfected after each use.

Such patient sensors may communicate with a patient monitor using a communication cable. For example, a patient sensor may use such a communication cable to send a signal, corresponding to a measurement performed by the sensor, to the patient monitor for processing. However, the use of communication cables may limit the range of applications available, as the cables may limit a patient's range of motion by physically tethering the patient to a monitoring device.

Although wireless patient sensors may transmit information without the need for a communication cable, the sensors may be bulky due to the number of components included in the housing. For example, wireless patient sensors typically employ batteries to power the device, and the sensors also include a wireless module in addition to the sensing devices and other related circuitry. Since batteries afford a limited power source, wireless patient sensors may only be operational for a limited window of time before the battery is depleted and must be recharged or replaced to continue sensor operation. Generally, a battery-powered sensor utilizes a removable battery, which results in a sensor housing with crevices and/or electrical connectors that may increase the difficulty of disinfection.

BRIEF DESCRIPTION OF THE DRAWINGS

Advantages of the disclosed techniques may become apparent upon reading the following detailed description and upon reference to the drawings in which:

FIG. 11 is a block diagram of the components of an example of a forehead pulse oximetry sensor, in accordance with an embodiment;

FIGS. 12A&B are perspective views of the forehead pulse oximetry sensor of FIG. 11 being applied to a patient, in accordance with an embodiment;

FIG. 15 is a perspective view of a patient monitoring system configured to remotely monitor a physiological parameter of the patient, and including an embodiment of the pulse oximetry sensor of FIGS. 1A-1C and a patient monitor, in accordance with an embodiment;

DETAILED DESCRIPTION OF SPECIFIC EMBODIMENTS

Figure 1A:
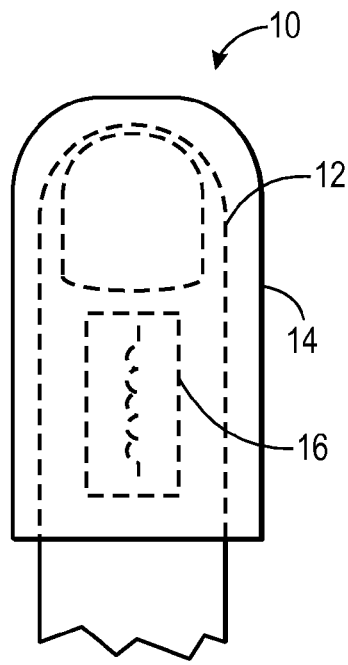
FIGS. 1A-1C are top, bottom, and side views, respectively, of a pulse oximetry sensor, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain circumstances, it may be desirable for a reusable sensor to have a housing which facilitates efficient and thorough disinfecting. For example, as discussed above, it may be desirable for a reusable, wireless pulse oximetry sensor to have a rechargeable battery that is encapsulated by the housing in order to minimize or eliminate the number of crevices in the housing and/or electrical connectors. Furthermore, while a wireless sensor allows a greater range of motion for a patient, the wireless sensor may be bulky and interfere with routine tasks of the patient. Accordingly, it may also be desirable to minimize the size of the internal components of the sensor to maximize the ease of use of the sensor with the patient.

With the foregoing in mind, previously described wireless sensors, such as those used for pulse oximetry, generally lacked an encapsulating housing to facilitate disinfection. To address this issue, the present embodiments describe a wireless sensor that is equipped with a rechargeable battery and an inductive charging coil to enable recharging of the sensor without removing the battery and without having to plug the sensor into a charging station via an electrical connector. In the disclosed embodiments, the sensor may also be designed to enable the wireless transfer of detector signal data measured by the sensor. Embodiments such as these are discussed below with respect to FIGS. 1A-1C and FIGS. 11-14.

Given that reusable sensors are disinfected after each use, it may be desirable to recharge the sensor while disinfecting to minimize the time that the sensor is unavailable for use. As such, the present embodiments describe a system for charging and disinfecting one or more sensors at the same time and in one enclosure. Furthermore, because the described system charges a rechargeable battery of the sensor via inductive charging, the circuitry and the rechargeable battery of the sensor may be fully enclosed. As such, a variety of disinfecting agents, including disinfecting solutions, are suitable for the system. Embodiments such as these are discussed below with respect to FIGS. 2-4 and 6, and these approaches may also be used alone or in any combination as discussed with respect to FIGS. 1A-1C and FIGS. 11-14. Other embodiments that describe techniques for charging and disinfecting a sensor are discussed in detail with respect to FIGS. 7-10.

Furthermore, in certain embodiments it may be desirable for a wireless sensor to perform minimal signal processing in order to reduce the size of the internal components of the sensor. Accordingly, the sensor may include an analog-to-digital converter for digitizing an analog electrical signal from its detector and a wireless module to transmit the digital signal to a patient monitor for further processing, e.g., for the calculation of a physiological parameter of the patient.

Additionally, it may be desirable to monitor changes in the physiological parameter of the patient from a remote monitor. For example, in a medical setting, it may not be feasible for a caregiver to continuously monitor the patient in the patient's room. To address this issue, monitoring of the patient may occur outside the patient room from a monitor at a central nurses' station, for example. To identify the digital signal transmitted by the sensor to the remote monitor, the sensor may also transmit identification data. For example, the sensor may include sensor identification data to send to the monitor. Additionally, the sensor also may send identification data for the current patient, so that the digital signal may be linked to the appropriate patient on the remote monitor. Accordingly, it may be desirable to provide a system in which a wireless, reusable sensor may be linked to a specific patient, and the physiological parameter may be monitored at a remote monitor. Embodiments such as these are discussed below with respect to FIGS. 15-18. Additionally, a method for linking a wireless, reusable sensor with a specific patient is discussed below with respect to FIG. 19. These approaches may also be used alone or in any combination with respect to FIGS. 1-14.

Figure 1B:
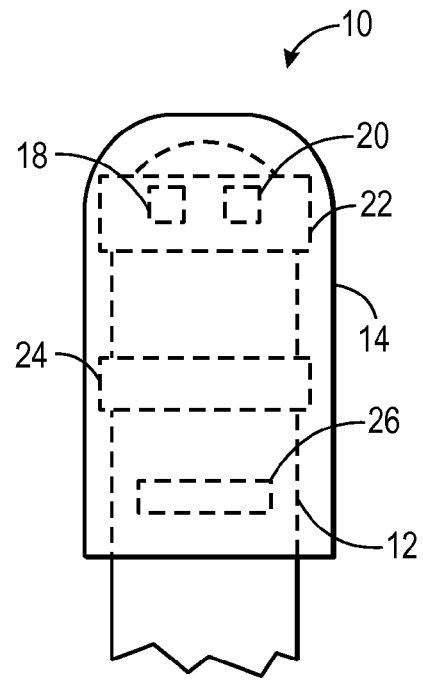
Figure 1C:
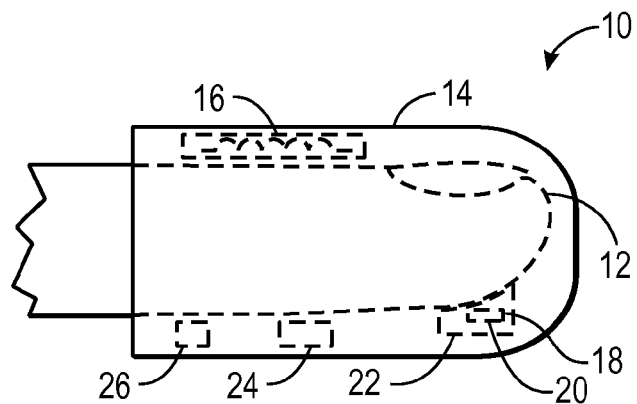

With the foregoing in mind, FIGS. 1A-1C illustrate top, bottom, and side views, respectively, of an embodiment of a wireless sensor 10. In the embodiments discussed below, the sensor 10 is presented as a pulse oximetry sensor by way of example, but is should be understood that other types of sensors may similarly benefit from the techniques discussed herein. The sensor 10 includes a housing 14, which is adapted to fit about a tissue of a patient 12. Pulse oximetry sensors may be placed on a patient in a location that is normally perfused with arterial blood to facilitate measurement of desired physiological parameters, such as arterial oxygen saturation measurement ($SpO_2$). For example, common sensor sites include a patient's fingertips, toes, earlobes, or forehead. Although the illustrated embodiment depicts a finger of a patient, it is to be understood that the sensor 10 may be easily adapted to fit about any number of tissue regions of the patient. As shown, the housing 14 may be tubular to fit about the finger of the patient 12. Additionally, the housing 14 may be boot-shaped such that the housing 14 may be elongated about the length finger of the patient and wider and/or thicker about the end corresponding to the fingertip of the patient 12 (e.g., a square end).

To acquire a signal corresponding to one or more physiological parameters of the patient 12, the sensor 10 may include one or more emitters 18 and one or more detectors 20. The emitter 18 and the detector 20 are disposed in the housing 14 and are electrically coupled to circuitry 22. For pulse oximetry applications, the emitter 18 may transmit light at certain wavelengths (e.g., RED light and/or IR light) into the tissue, wherein the RED light may have a wavelength of about 600 to 700 nm, and the IR light may have a wavelength of about 800 to 1000 nm. In other applications, a tissue water fraction (or other body fluid related metric) or a concentration of one or more biochemical components in an aqueous environment may be measured. As such, the emitter 18 may transmit two or more wavelengths of light, most commonly near infrared wavelengths between about 1,000 nm to about 2,500 nm. The detector 20 may be a photodetector selected to receive light in the range emitted from the emitter 18 after it has passed through the tissue. The emitter 18 and the detector 20 may operate in various modes (e.g., reflectance or transmission). The circuitry 22 may include an analog-to-digital converter for digitizing the electrical signal received from the detector 20. As should be appreciated, however, the circuitry 22 may also include additional components for further signal processing or calculating a physiological parameter from the signal.

In particular embodiments, the sensor 10 is capable of communicating wirelessly. For example, to transmit the signal related to a physiological parameter, the sensor 10 may include a radio-frequency transceiver 26. As described above, the RF transceiver 26 may transmit a raw digitized detector signal, a processed digitized detector signal, and/or a calculated physiological parameter, as well as any data that may be stored in the sensor 10 as discussed below. For example, in certain embodiments, the circuitry 22 may include a signal processing component configured to calculate one or more parameters of interest (e.g., oxygen saturation) to reduce the amount of information transmitted by the RF transceiver 26. That is, the RF transceiver 26 may only transmit one or more parameters received from a signal processing component rather than the raw or processed digitized detector signal. The RF transceiver 26 may establish wireless communication with a wireless receiver (e.g., a patient monitor, a multi-parameter patient monitor, or a wireless access point) using any suitable protocol. In the illustrated embodiment, the RF transceiver 26 wirelessly transmits data by digital radio signals. However, in certain embodiments, the sensor 10 may include any number of wireless modules, which may be capable of communications using the IEEE 802.15.4 standard, and may be, for example, ZigBee, WirelessHART, or MiWi modules. Additionally or alternatively, the wireless module may be capable of communicating using the Bluetooth standard, one or more of the IEEE 802.11 standards, an ultra-wideband (UWB) standard, or a near-field communication (NFC) standard. In the illustrated embodiment, the wireless module may be the RF transceiver 26 that may be capable of longer range transmission and may be capable of communicating with a radio-frequency identification (RFID) tag of a patient. Additionally, the sensor 10 may be part of a sensor network, where the sensor 10 measures a particular variable (e.g., oxygen saturation), while another sensor measures a variable it is ideally suited for. An example may be measuring heart rate with a wireless sensor, and transmitting the heart rate and timing information to the sensor 10. As such, the sensor 10 does not have to calculate heart rate, thus alleviating the sensor 10 from activating the emitters 18, which can be a power-savings measure.

The RF transceiver 26 may be desirable as it allows the sensor 10 to communicate with a monitor without a cable. For example, the interface between a sensor and a cable may have one or more crevices, resulting from the method used to connect the cable to the sensor. As previously described, sensors with crevices or electrical connectors in the housings may be more difficult to disinfect. Accordingly, the sensor 10, which wirelessly transmits signals via RF transceiver 26, may minimize the number of crevices in the housing 14.

To facilitate efficient disinfecting of the sensor 10, the housing 14 may be formed from any suitable material that can be disinfected and can be shaped to minimize or eliminate crevices. Additionally, the housing 14 may be formed from a material that may protect the components of the sensor 10 from a variety of disinfecting agents (e.g., disinfecting solution, disinfecting gas, or UV light). In particular, the housing 14 may be resistant to or may prevent fluid infiltration. For example, the housing 14 may be formed from rigid or conformable materials, such as rubber or elastomeric compositions (including acrylic elastomers, polyimide, silicones, silicone rubber, celluloid, PMDS elastomer, polyurethane, polypropylene, acrylics, nitrile, PVC films, acetates, and latex). Further, the sensor 10 may be formed from molded or overmolded components.

Additionally, it may be desirable for the housing 14 to encapsulate the components of the sensor 10 such that no components are designed to be removable or connected to an electrical connector. For example, wireless sensors generally include a battery to power the device, however batteries typically must be recharged or replaced as the battery depletes with use. Removing a battery to replace or recharge the battery may require a door and a hinge in a housing of a device. Alternatively, recharging a battery without removing it may require an electrical connector. Either design may result in several crevices in the housing 14 that are difficult to disinfect.

For the reasons described above, the sensor 10 may include a rechargeable battery 24 connected to an inductive charging coil 16. The battery 24, for example, may be a lithium ion, lithium polymer, nickel-metal hydride, or nickel-cadmium battery. The battery 24 may be a bulky component of the sensor 10. Accordingly, it may be desirable to select a smaller battery and recharge more frequently. The inductive charging coil 16 may facilitate recharging without the removal of the battery 24. In certain embodiments, the inductive charging coil 16 may include a plurality of windings of electrically conductive wire to receive energy from an electromagnetic field and convert the energy into electric current, which may be used to charge battery 24. In certain embodiments, the inductive charging coil 16 may be positioned in the housing 14 such that a user may easily align the sensor 10 with a charging device containing an induction coil for generating the electromagnetic field. It is to be understood that the position of the inductive charging coil 16 may be easily adjusted to more closely align with an inductive coil of a particular charging device. For example, the sensor 10 and the charging device may also include magnets to facilitate the aligning of the respective inductive coils and maximize the efficiency of the energy transfer.

Figure 2:
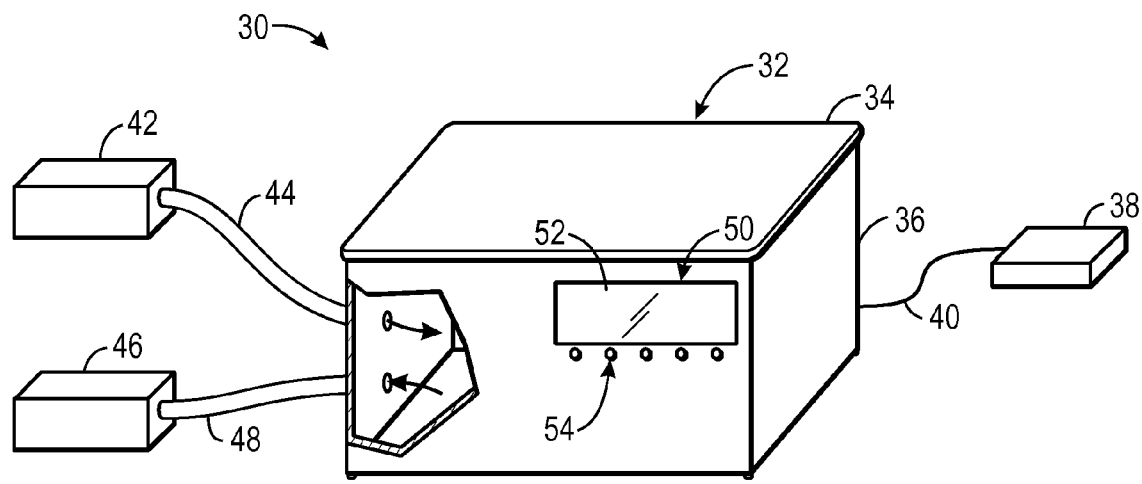
FIG. 2 is a perspective view of a system, including a charging and disinfecting device for charging and disinfecting the sensor of FIG. 1, in accordance with an embodiment.

Turning to FIG. 2, a perspective view of a system 30 that may be operable for charging and disinfecting the sensor 10 or a variety of other medical devices equipped with an inductive coil is illustrated in accordance with an embodiment. The system 30 includes a charging and disinfecting device 32. In certain embodiments, the device 32 may be a sealable enclosure. For example, the device 32 may include a housing 36 and a sealable lid 34. The sealable lid 34 may be closed manually or automatically. The housing 36 and the sealable lid 34 may be constructed from any number, and any combination, of suitable materials, including, but not limited to, plastic, metal, or glass. In certain embodiments, the device 32 may be configured to be used with one or more disinfecting agents (e.g., a disinfecting solution or gas). Alternatively or additionally, the device 32 may include a UV-penetrable region, as well as reflective surfaces for directing UV light.

The device 32 may include an inlet for receiving a disinfecting agent. It should be appreciated that there are a variety of disinfecting agents suitable for disinfecting medical devices, as well as a variety of methods of supplying the disinfectants. Accordingly, it should be understood that the system 30 may be easily adapted to include more than one inlet. For example, a user may simply pour a disinfecting liquid into the device 32. As such, the inlet may be the opening in the housing 36 when the sealable lid 34 is open. Alternatively, the inlet may be a UV-penetrable region of the device 32 and a UV lamp disposed in the housing 36. In other embodiments, the disinfecting agent may be supplied via inlet tubing 44, as illustrated in FIG. 2. The inlet tubing 44 may be coupled to a disinfecting agent supply unit 42, which houses the disinfecting agent. Additionally, the device 32 may include an outlet for removing the disinfecting agent after the completion of disinfecting and charging cycle. In certain embodiments, the outlet may include outlet tubing 48, which may be coupled to a disinfecting agent waste unit 46 or a drain. Furthermore, the inlet, outlet, or both may also include a valve (not shown), which may be adjusted manually or automatically to adjust the flow rate of the disinfecting agent into or out of the device 32.

Figure 3:
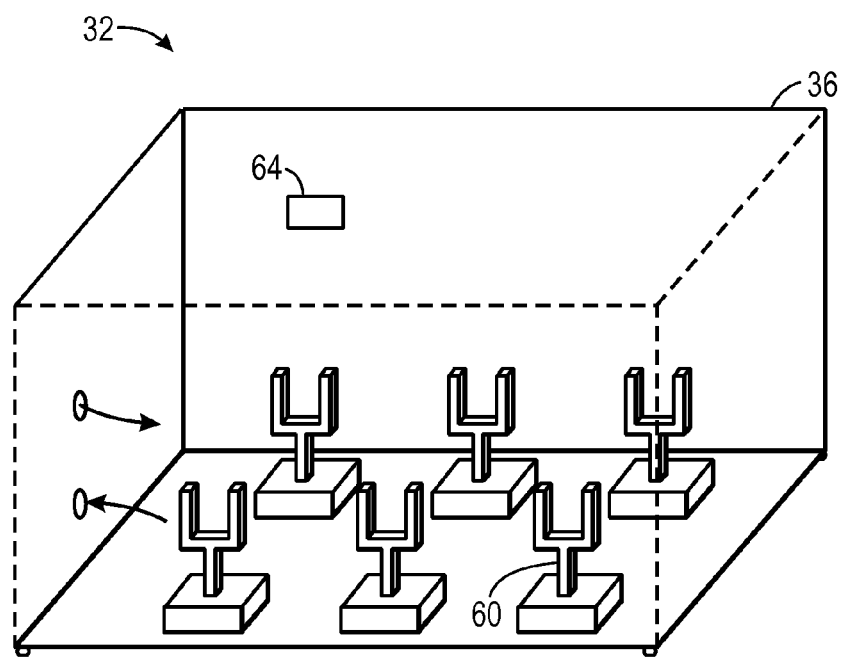
FIG. 3 is a perspective view of the charging and disinfecting device of FIG. 2, including a plurality of inductive stations, in accordance with an embodiment.

In the illustrated embodiment, the device 32 includes a control unit 50. The control unit 50 may include a processor (not shown) for monitoring the amount of disinfecting agent in the device 32. For example, the processor may adjust the previously mentioned valve or valves to adjust the influx and/or outflux of the disinfecting agent. In certain embodiments, the processor may communicate with a level sensor 64, as shown in FIG. 3, which measures the amount of the disinfecting agent in the device 32. The level sensor 64 may be a gas level sensor or a liquid level sensor. The control unit 50 may also include a memory unit (not shown), a display 52 to present information to the user, and input components 54 (e.g., buttons, switches, or knobs). The control unit 50 may be powered by an external main power supply 38 via a wired connection 40. The main power supply 38 may be a battery or an electrical outlet, for example.

The main power supply 38 also supplies power to one or more inductive stations 60 of the device 30, as illustrated by FIG. 3, which depicts internal components of an embodiment of the device 30. Each inductive station 60 may be shaped to hold and position respective sensors 10. As illustrated, each inductive station 60 may be a vertical two-prong assembly, for example. It should be appreciated, however, that a variety of geometries may be suitable and may be designed for positioning a specific type of sensor 10. For example, the inductive station 60 may be rod-shaped, three-pronged, or flat, and may include an attachment to secure the sensor 10 to the inductive station 60. In other embodiments, the inductive station 60 may include a motor or hinge to rotate the sensor 10 to promote flow of a disinfecting solution around the sensor 10. Additionally, certain embodiments may include an additional method of disinfectant agitation to promote flow and/or distribution of a disinfecting agent around the sensor 10 (e.g., a rotor or a fan disposed in the device 32).

Figure 4:
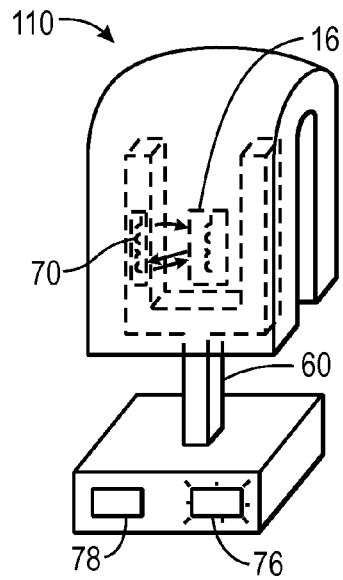
FIG. 4 is a perspective view of an inductive station of FIG. 3, in accordance with an embodiment.

Referring additionally to FIG. 4, to recharge one or more sensors 10, the inductive station 60 may also include one or more primary inductive coils 70. For example, in the illustrated two-prong embodiment of FIG. 3, one of the prongs may include a primary inductive coil 70. The inductive coil 70 may include a plurality of windings of electrically conductive wire to receive electrical power from the main power supply 38. The inductive coil 70, when coupled to the main power supply 38, creates an electromagnetic field which may induce an electrical current in the inductive charging coil 16 of the sensor 10. As previously described, the geometry of the inductive station 60 may position the primary inductive coil 70 and the inductive charging coil 16 in operational proximity, whereby the primary inductive coil 70 may induce an electrical current in the inductive charging coil 16. Also, the inductive station 60 and/or the sensor 10 may include magnets (not shown) to facilitate alignment of the inductive coil 70 with the inductive charging coil 16 to maximize the efficiency of the inductive power transfer. Additionally or alternatively, the inductive station 60 may be at least partially composed of ferrite to facilitate magnetic coupling between the inductive coil 70 and the inductive coil 16.

In addition to charging the sensors 10, the device 30 may communicate with the sensors 10 via inductive data transfer. For example, the sensor 10 may communicate information relating to sensor health to the device 32. Specifically, the sensor 10 may communicate that it is not functioning properly or the battery 24 is finished charging. Additionally, in certain embodiments, the sensor 10 may store a value for the number of times the battery 24 has been charged, the number of times the sensor 10 has been disinfected, or both. The value may be stored in a memory unit of the sensor 10 or may be a count of an iteration counter of the sensor 10. Generally, reusable sensors have a maximum number of times they may be recharged, as rechargeable batteries often decay over time. Similarly, reusable sensors may have a limited lifetime or a maximum number of disinfecting cycles the sensors can withstand. Accordingly, a monitor may determine the number of times the sensor 10 has been recharged or disinfected.

The device 30 may download this information from the sensor 10 and provide a user-perceivable indication to the user that the sensor 10 has reached a preselected maximum for the number of charging and disinfecting cycles or that the sensor 10 is not functioning properly. For example, the information may be available to the user on the display 52. The sensor of interest may be identified on the display 52 by the corresponding inductive station 60, which may be numbered. Alternatively or additionally, the inductive station 60 may provide a user-perceivable indication such as a green indicator 76 for a healthy sensor and a red indicator 78 for a problem sensor, or simply a light that turns on or flashes when there is a problem with the sensor 10.

Figure 5:
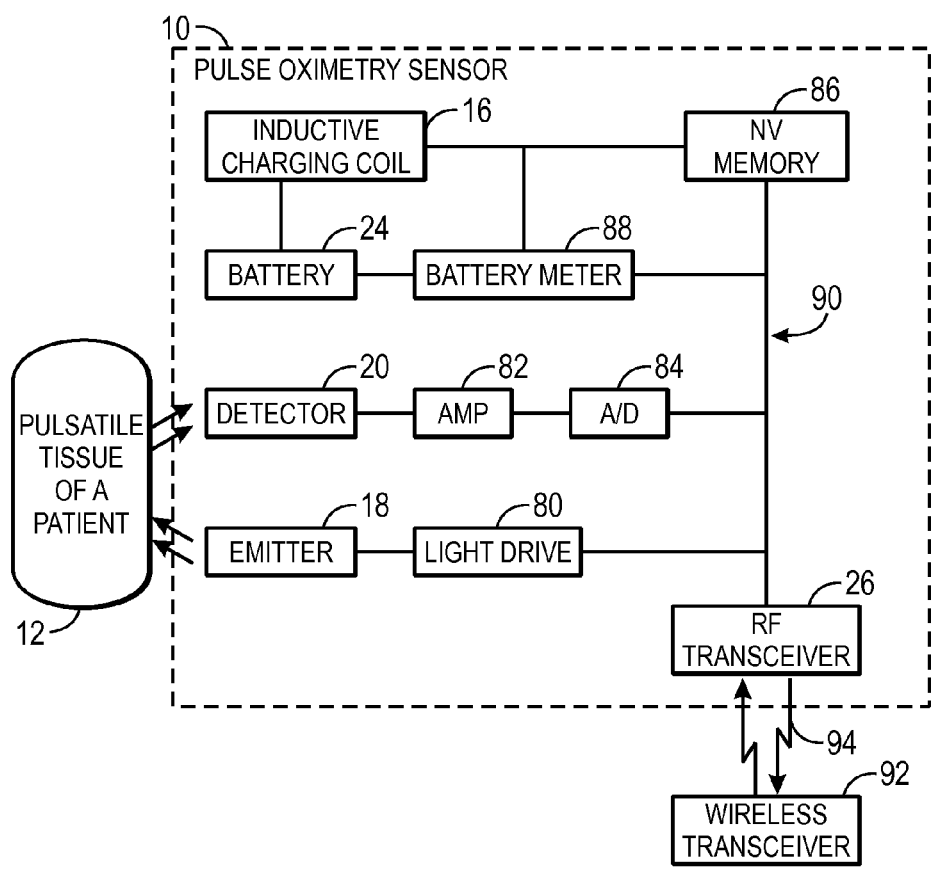
FIG. 5 is a block diagram of the components of an example of the pulse oximetry sensor of FIG. 1, in accordance with an embodiment.

As previously discussed, in addition to being configured for charging and disinfecting via the system 30, the sensor 10 may also be configured to generate a physiological parameter signal of the patient 12. In accordance with one embodiment, FIG. 5 illustrates a plurality of components that may be present within the housing 14 of the sensor 10 to facilitate the acquisition, processing, and transmission of the physiological parameter data. The wireless module 26 may receive control signals from a monitor via a wireless transceiver 92. The sensor 10 may also include a light drive 80 configured to drive the emitter 18 based on the control signals to emit light into the tissue 12. The detector 20 may detect the light after it has passed through the tissue 12. The received signal from the detector 20 may be passed through an amplifier 82 and an analog-to-digital (A/D) converter 84 for amplifying and digitizing the electrical signals from the sensor 10. The digital data may then be stored in a non-volatile (NV) memory 86, which may be coupled to the main system bus 90. Additionally, the NV memory 86 may also store historical data and/or values (e.g., detector signal data, data points, trend information) for the physiological parameter of the patient. For example, the NV memory 86 may store information regarding the wavelength of one or more light sources of the emitter 18, which may be sent to a patient monitor to allow for selection of appropriate calibration coefficients for calculating a physiological parameter (e.g., blood oxygen saturation). In the illustrated embodiment, the signal processing may be somewhat minimal to reduce the number of internal components of the sensor 10 and reduce bulkiness. However, certain embodiments may include additional or more complex signal processing or may calculate a physiological parameter from the detector signal data, which will be described in detail below with respect to FIG. 19.

In addition to communicating with a patient monitor, the sensor 10 may also communicate with the charging and disinfecting device 32. As described above, the NV memory 86 may store values corresponding to the number of times the sensor 10 has been recharged and/or disinfected. These values may be downloaded by the device 32 via inductive data transfer. In certain embodiments, the sensor 10 may also include a battery meter 88 to provide the expected remaining power of the battery 24 to the device 32 via inductive data transfer.

Figure 6:
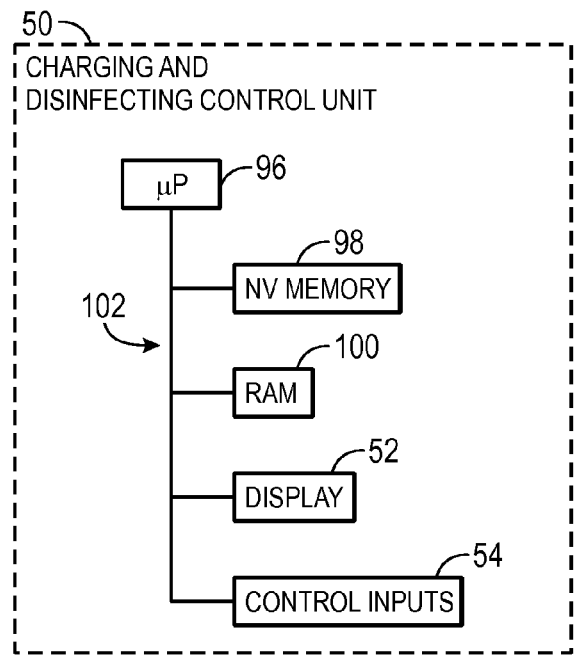
FIG. 6 is a block diagram of the components of an example of the control unit of the charging and disinfecting device of FIG. 2, in accordance with an embodiment.

To facilitate the processing and display of the data downloaded from the sensor 10, the device 32 may include the control unit 50, which may include a plurality of components as illustrated by FIG. 6, in accordance with an embodiment. For example, the control unit 50 may include a microprocessor 96 which may be coupled to a main system bus 102, which is also coupled to a NV memory 98, a RAM 100, a display 52, and control inputs 54. The display 52 may provide information to a user regarding the status of the sensor 10 (e.g., battery meter, number of recharges, or number of disinfecting cycles). Further, the display 52 may provide a recommendation to replace one or more sensors 10. For example, the control unit may determine that a sensor 10 should be replaced based at least in part upon the information regarding the status of the sensor 10. Additionally, the display 52 may also provide information regarding the disinfecting and charging cycle (e.g., disinfection agent selected, percent of cycle completed, or time remaining). The control inputs 54 may enable an operator to adjust the settings of the system 30.

The microprocessor 96 of the control unit 50 generally controls the operation of the device 32. The microprocessor 96 may also control the supply of power from the main power supply 38 to the inductive station 60. In an embodiment, NV memory 98 may include one or more sets of instructions to be executed by the microprocessor 96 for carrying out the charging and disinfecting techniques described herein. That is, as described above, based at least in part on the sensor data inductively downloaded from the sensor 10, the microprocessor 96 may compare one or more values, corresponding to the number of charging or disinfecting cycles, stored in a memory unit of the sensor 10 to a maximum value that may be stored in NV memory 98. Additionally, the NV memory 98 and/or RAM 100 may store user preferences and various operational parameters of the device 32. For example, the NV memory 98 may store information regarding the disinfecting agents, which may allow for the selection of appropriate disinfecting durations. As described previously, the device 32 may include a solenoid valve (not shown) coupled to inlet tubing 44. Accordingly, the microprocessor 96 may calculate the appropriate time for the disinfecting agent to enter the device 32 and may close the solenoid valve after the appropriate time. Additionally or alternatively, the microprocessor 96 may control other inlets for receiving a disinfecting agent, such as a UV lamp disposed in the device 32.

Figure 7:
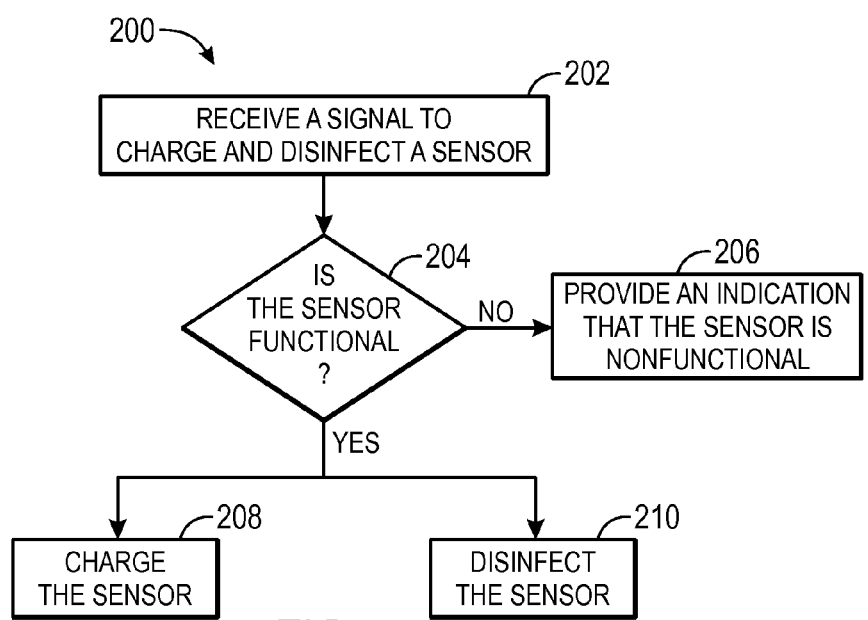
FIG. 7 is a flowchart illustrating a process for charging and disinfecting a pulse oximetry sensor, in accordance with an embodiment.
Figure 8:
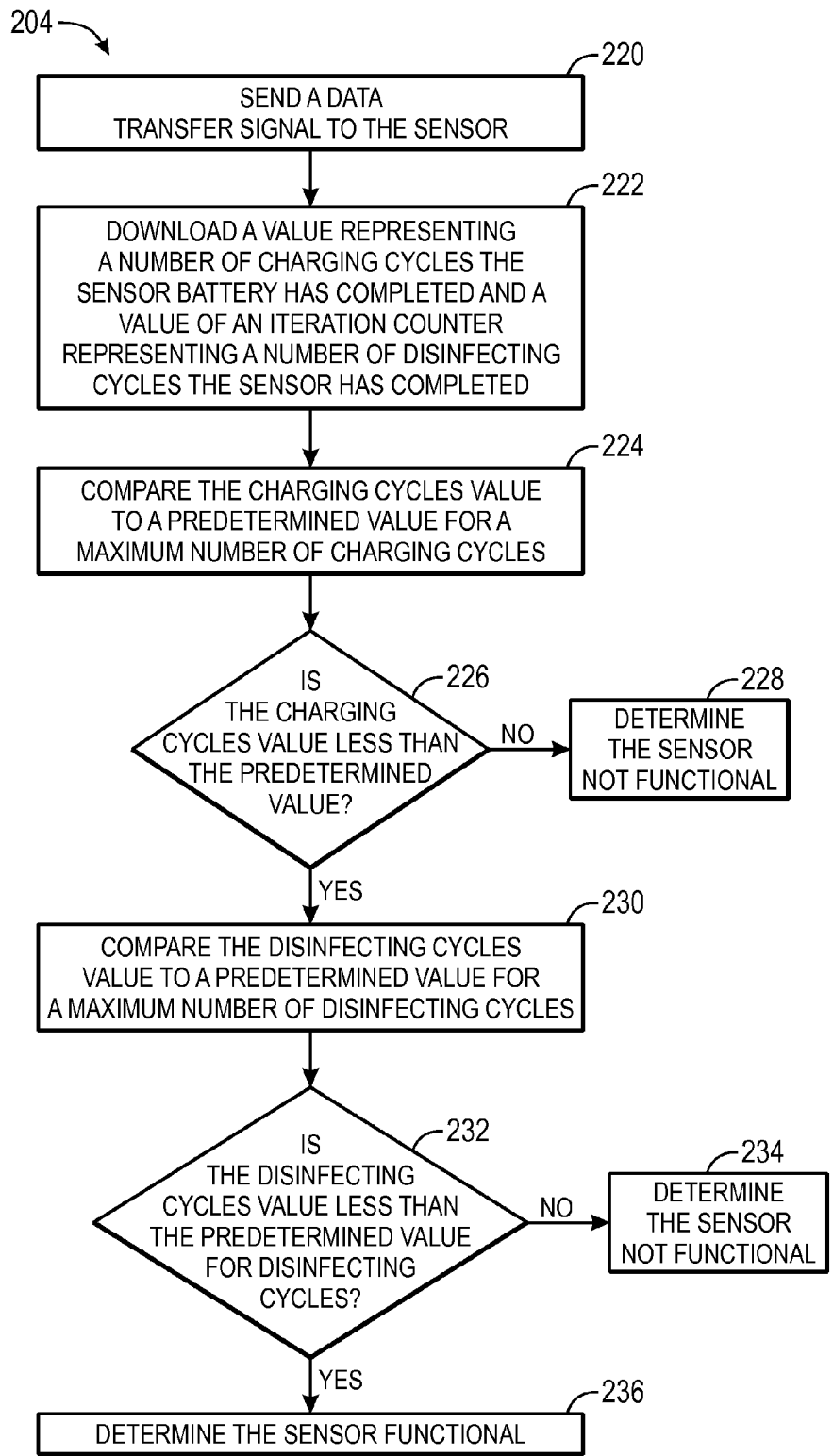
FIG. 8 is a flowchart illustrating a process for determining whether the pulse oximetry sensor is functional, in accordance with an embodiment.

Accordingly, there are various processes, which may be performed by the control unit 50, for a variety of disinfecting agents. For example, FIG. 7 illustrates a high-level block diagram of an embodiment of a process 200 by which the control unit 50 may charge and disinfect the sensor 10. First, the control unit 50 receives a signal instructing the control unit 50 to charge and disinfect the sensor 10 (block 202). The signal may be a user-provided indication (e.g., via control inputs 54). In the illustrated embodiment, the control unit 50 may determine whether the sensor is still functional and/or is eligible for charging and disinfecting (block 204), which will be described in detail below. If the sensor 10 is not eligible for charging and disinfecting, the control unit 50 may provide an indication that the sensor 10 is nonfunctional (block 206). In one embodiment, the control unit 50 may indicate the nonfunctional sensor 10 by turning on the red indicator 78 at the corresponding inductive station 60. Additionally or alternatively, the display 52 may provide the indication, which may include an error message and/or an identifying number related to the corresponding inductive station 60. However, if the sensor 10 is eligible, the control unit 50 may charge and disinfect the sensor 10 (blocks 208 and 210).

Inductive coupling may also be used for communication, as well as charging. As such, in determining whether the sensor 10 is functional or eligible for charging and disinfecting, the control unit 50 may communicate with the sensor 10 via inductive data transfer. It should also be appreciated that in addition to, or instead of, communicating via inductive data transfer, the control unit 50 may include an RF transceiver for communicating with the RF transceiver 26 of the sensor 10. The eligibility assessment of the sensor 10 may be performed according to the process 204 illustrated in FIG. 8, as described in detail below. The control unit 50 may send a data transfer signal to the sensor 10 to initialize the inductive data transfer 74 (block 220). As such, the control unit 50 may download information regarding the health of sensor 10 and/or values stored in the NV memory 86 regarding the number of times the sensor 10 has been recharged or disinfected (block 222). The values stored in the NV memory 86 may be values of iteration counters. The control unit 50 may then compare the value representing the number of recharges to a predetermined value for the maximum number of recharges, which may be stored in the NV memory 98 of the control unit 50 and/or may be downloaded from the sensor 10 (block 224). The number of recharges may be an indication of the health of the battery 24, as rechargeable batteries often decay after repeated recharging. If the value is higher than the predetermined value (block 226), the control unit 50 may determine that the sensor 10 is nonfunctional (block 228). Similarly, the control unit 50 may compare the value representing the number of disinfecting cycles to a predetermined value (block 230). Reusable pulse oximetry sensors may have a limited lifetime or a maximum number of disinfecting cycles associated with the integrity of the sensor components. As such, the disinfecting value may be indicative of the health of sensor 10. If the value is higher than the predetermined value (block 232), the control unit 50 may determine that the sensor 10 is nonfunctional (block 234). Accordingly, if both values are within the allowable range, the control unit 50 may determine that the sensor 10 is functional and eligible for charging and disinfecting (block 236).

Figure 9:
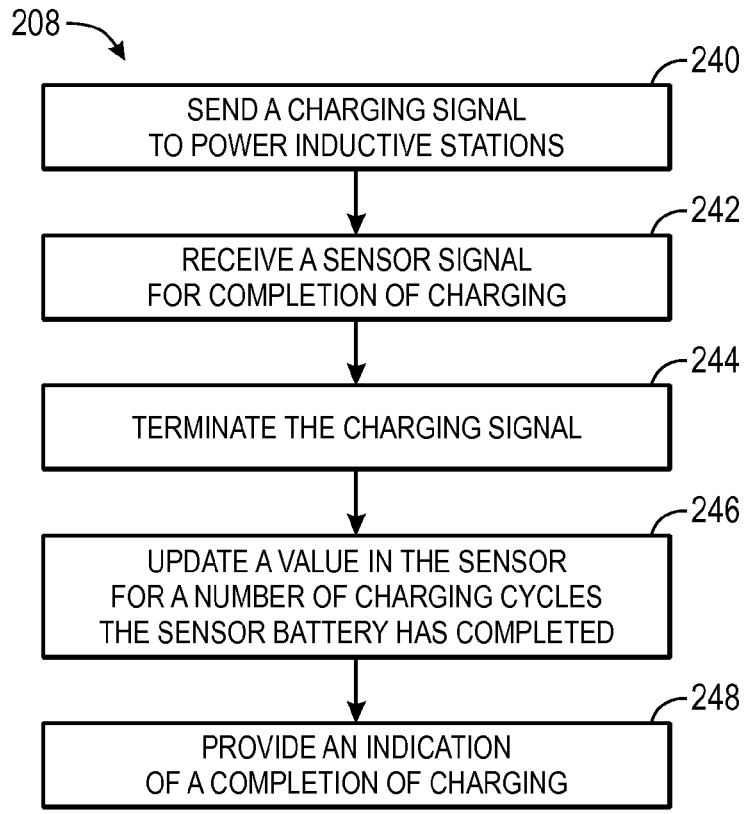
FIG. 9 is a flowchart illustrating a process for charging the pulse oximetry sensor, in accordance with an embodiment.
Figure 10:
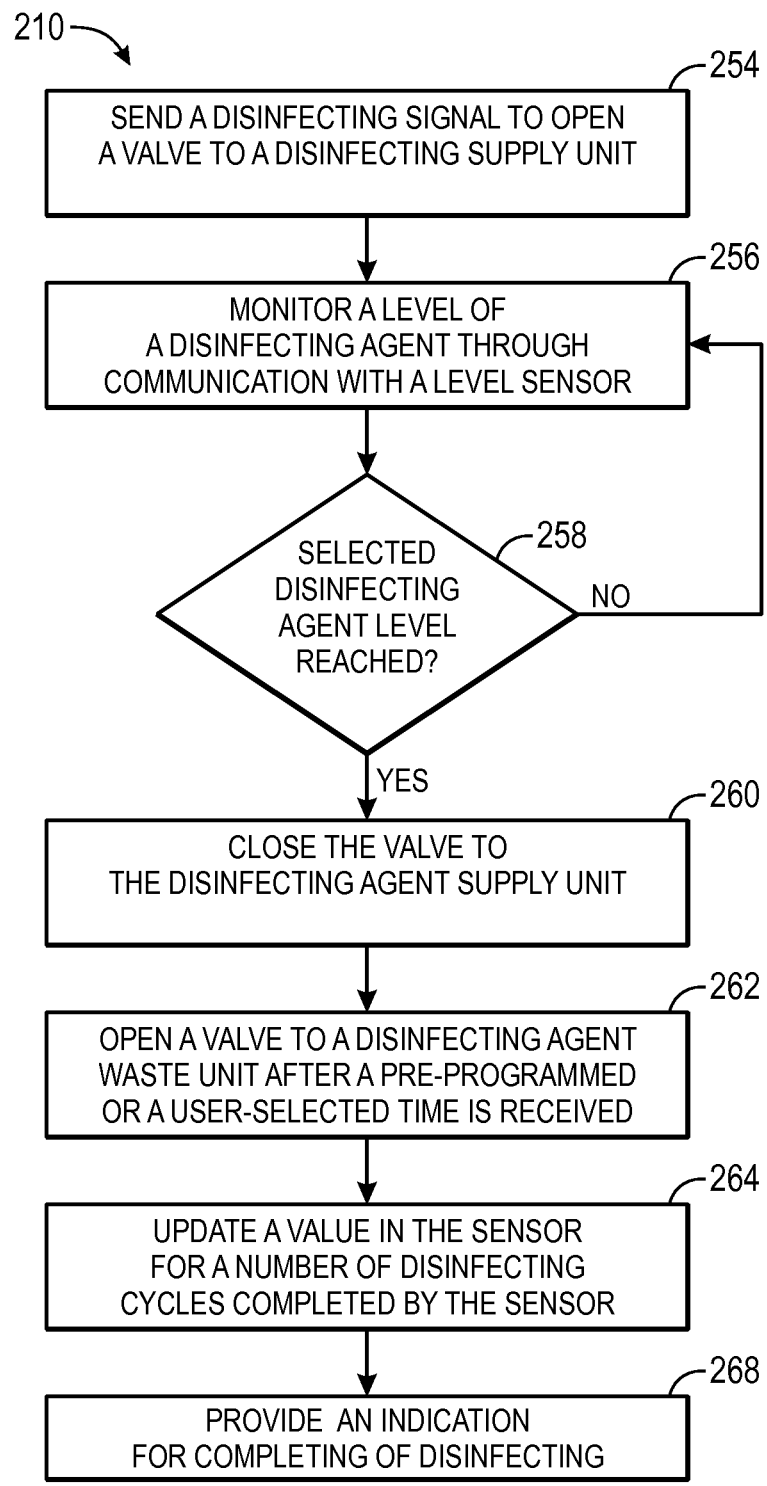
FIG. 10 is a flowchart illustrating a process for disinfecting the pulse oximetry sensor, in accordance with an embodiment.

To begin recharging the sensor 10, the control unit 50 may send a charging signal to direct the power from the main power supply 38 to the inductive station 60 (block 240), as illustrated in FIG. 9. The electrical power runs through the primary inductive coil 70 of the inductive station 60 and produces an electromagnetic field which induces an electrical current in the inductive charging coil 16 of sensor 10. The sensor 10 may use the electrical current to recharge the battery 24. When the battery 24 is fully charged, the control unit 50 may receive a signal from the sensor 10 for the completion of charging (block 242). For example, the battery meter 88 may provide an indication that charging is completed. Then, the control unit 50 may terminate the charging signal to prevent the supply of power to the inductive station 60 (block 244). Additionally, in certain embodiments, the control unit 50 may send a signal to the sensor 10 instructing the sensor 10 to update the iteration counter, or the value stored in NV memory 86, for the number of recharges (block 246). The control unit 50 may also provide a user-perceivable indication of the completion of charging (block 248). For example, the display 52 or the inductive station 60 may provide an indication (e.g., text, a beep, or a light).

The system 30 may also disinfect the sensor 10 simultaneously with charging the sensor 10. As such, a portion of the charging cycle and a portion of the disinfecting cycle may overlap. The disinfecting cycle may be performed according to the process 210 illustrated by FIG. 10, as described in detail below. The control unit 50 may send a disinfecting signal to open a valve to a disinfecting agent supply unit 42 to receive a disinfecting agent into the device 32 (block 254). The control unit 50 may monitor the level of the disinfecting agent through communication with the level sensor 64, which measures the amount of disinfecting agent in the device 32 (block 256). If the level sensor 64 communicates that the desired level of disinfecting agent is reached, then the control unit 50 may close the valve to the disinfecting agent supply unit 42 (blocks 258 and 260). Additionally or alternatively, the microprocessor 96 may calculate the time appropriate for receiving the disinfecting agent, based in part by values stored in the NV memory 98, and may close the valve to the disinfecting agent supply unit 42 after the appropriate duration (block 260). In certain embodiments, the control unit 50 may send a signal to the sensor 10 instructing the sensor 10 to update the iteration counter, or the value stored in NV memory 86, for the number of disinfecting cycles completed (block 262). Additionally, the control unit 50 may provide a user-perceivable indication of the completion of charging (block 268). For example, the display 52 or the inductive station 60 may provide an indication (e.g., text, a beep, or a light).

While embodiments for the system 30, as illustrated in FIGS. 2-4, and the process 200 of charging and disinfecting a pulse oximetry sensor, as illustrated in FIGS. 7-10, described above may be applicable to the embodiment of the sensor 10, as illustrated in FIGS. 1A-1C, additional or alternative embodiments of a wireless, reusable pulse oximetry sensor may be considered. For example, as previously described, the sensor 10 may be easily adapted to fit adjacent to any number of pulsatile tissue regions of the patient. The embodiment of sensor 10, as illustrated by FIGS. 1A-1C, specifically depicts the sensor 10 in use with a digit of a patient. However, the housing 14 may be adapted to fit adjacent to a different region of pulsatile tissue of the patient, such as a forehead of the patient of an earlobe of the patient. Similarly, the one or more inductive stations 60 of the charging and disinfecting device 32 may be adapted to appropriately position a plurality of sensors 10 with same or different functionalities. As such, the internal components of the sensor 10 and/or the charging and disinfecting device 32 may remain unchanged.

Turning to FIG. 11, a block diagram of a pulse oximetry sensor 280 is illustrated in accordance with an embodiment. The pulse oximetry sensor 280 may include the emitter 18, the detector 20, the related circuitry 22, the rechargeable battery 24, the inductive charging coil 16, and the RF transceiver 26 of the sensor 10. However, in the illustrated embodiment, the sensor 280 may be configured to be placed on the forehead of the patient and may include a housing 282. The housing 282 may be formed from the same selection of suitable materials as the housing 14, and may similarly encapsulate the components of the sensor 280. However, the housing 282 may also include an adhesive or other gripping surface configured to secure the sensor 280 to the skin of the forehead 292 of the patient 290, as shown in FIG. 12A. The sensor 280 may be placed above the eye or any suitable location, such as another cerebral location or a somatic location, or a combination. For example, the sensor 280 may be placed on the patient's stomach, chest, back, or similar location. Additionally or alternatively, the sensor 280 may be positioned on the patient 290 and may be secured by a headband 294, as shown in FIG. 12B.

Figure 13:
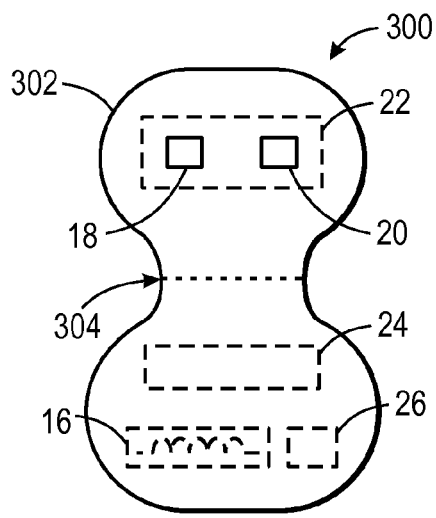
FIG. 13 is a block diagram of the components of an example of an ear pulse oximetry sensor, in accordance with an embodiment.
Figure 14A:
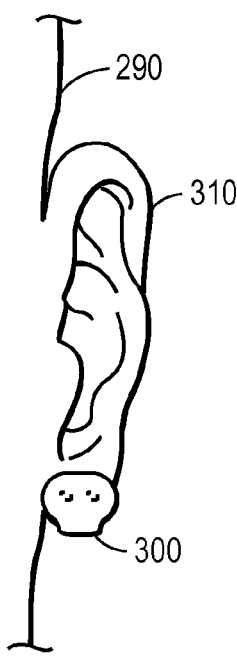
FIGS. 14A&B are perspective views of the ear pulse oximetry sensor of FIG. 13 being applied to the patient, in accordance with an embodiment.
Figure 14B:
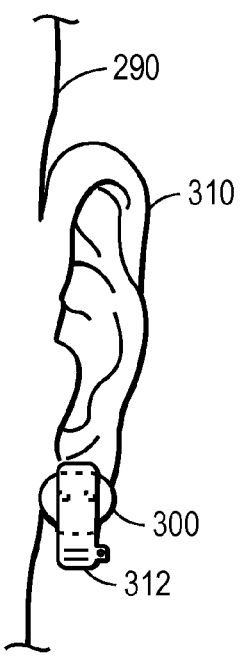

Similarly, the housing of a pulse oximetry sensor may be adapted to fit about an earlobe of the patient. For example, FIG. 13 illustrates a block diagram of a pulse oximetry sensor 300 in accordance with an embodiment. As previously described, the pulse oximetry sensor 300 may include the same internal components as sensor 10 and sensor 280, such as the emitter 18, the detector 20, the related circuitry 22, the rechargeable battery 24, the inductive charging coil 16, and the RF transceiver 26. In the illustrated embodiment, the housing 302 is adapted to be bent about the earlobe of a patient via fold 304. While the illustrated embodiment depicts the sensor 300 as substantially symmetrical about the fold 304, alternative configurations may be considered. The housing 302 may also include an adhesive of other gripping surface configured to secure the sensor 300 to the skin of the ear 310 of the patient 290, as shown in FIG. 14A. Additionally or alternatively, the sensor 300 may be positioned on the patient 290 and may be secured by a clip 312, as shown in FIG. 14B. In certain embodiments, the housing 302 may be configured as the clip 312, such that the clip 312 includes the internal components of the sensor 300.

As previously described, it may be desirable to limit the size of the internal components of the sensor 10 to minimize bulkiness and maximize the ease of use with the patient. Accordingly, in certain embodiments, it may be desirable for the sensor 10 to wirelessly transmit the digital detector signal to a patient monitor, which may perform additional processing of the signal and calculate a physiological parameter of the patient. In certain circumstances, a healthcare provider may wish to monitor the changes in the physiological parameter at a remote monitor, such as a central nurses' station. Furthermore, remote monitoring at one, or several, central stations may be more cost efficient. For example, the number of patient monitors, which are generally present with the pulse oximetry sensor in a corresponding patient room, may be reduced in a medical setting. Instead of calculating and displaying a physiological parameter with a patient monitor specific for each pulse oximetry sensor, a plurality of sensors may transmit signals to a central patient monitor for calculation and display.

A pulse oximetry monitor may communicate with one or more pulse oximetry sensors placed at different locations on the same patient. In addition, a pulse oximetry monitor is often directly connected to a sensor by a cable or is located near a patient wearing the sensor to facilitate wireless communication with the sensor. As such, a healthcare provider may be able to easily identify the physiological parameter displayed on the monitor with the correct patient even though the monitor may not display patient identification data with the physiological parameter. However, in embodiments in which the sensors 10 transmit signals without patient identification data to a central patient monitor for calculation and display, the healthcare provider may not be able to correctly identify the calculated physiological parameters with the corresponding patients.

With the foregoing in mind, FIG. 15 illustrates a perspective view of an embodiment of a patient monitoring system 350, including the sensor 10, a wireless receiver 352, a patient monitor 360, a multi-parameter monitor 366, and a patient identification bracelet 358. The patient monitor 360 is configured to enable the calculation of one or more physiological parameters of the patient 12 on the wireless sensor 10. The patient monitor 360 may include a display 362 and control inputs 364. Although the illustrated embodiment of system 350 is a pulse oximetry monitoring system, it should be noted that the patent monitoring system 350 may be configured to perform any number of measurements on a patient to determine one or more physiological parameters of the patient 12. That is, while the pulse oximetry monitoring system 350 may determine pulse rates and blood oxygen saturation levels (e.g., $SpO_2$ values) for a patient, the system 350 may, additionally or alternatively, be configured to determine a patient's respiration rate, glucose levels, hemoglobin levels, hematocrit levels, tissue hydration, regional saturation, as well as other physiological parameters.

In certain embodiments, it may be desirable to calculate and/or display the one or more physiological parameters using the multi-parameter monitor 366. For example, the patient monitor 360 may be communicatively coupled to the multi-parameter monitor 366 via a cable 370 connected to a sensor input port or via a cable 368 connected to a digital communication port. The multi-parameter monitor 366 may provide a central display 372 to facilitate the presentation of patient data, such as pulse oximetry data determined by system 350 and/or physiological parameters determined by other patient monitoring systems (e.g., electrocardiographic (ECG) monitoring system, a respiration monitoring system, a blood pressure monitoring system, etc.). For example, the multi-parameter monitor 366 may display a graph of $SpO_2$ values, a current pulse rate, a graph of blood pressure readings, an electrocardiograph, and/or other related patient data in a centralized location for quick reference by a medical professional. In addition to the monitor 360, or alternatively, the multi-parameter monitor 366 may be configured to calculate physiological parameters from the digital detector signal from the sensor 10. The multi-parameter monitor 366 may also include a processor configured to execute code. In addition, the patient monitor 360 and/or the multi-parameter monitor 366 may be connected to a network to enable the sharing of information, such as patient physiological data captured by the sensor 10, with servers or other workstations.

To link the sensor 10 with the corresponding patient identification data, the RF transceiver 26 of the sensor 10 may communicate with the patient identification bracelet 358 via wireless communication 354. Accordingly, the RF transceiver 26 may include an antenna to transmit and receive radio signals and additionally may include a reader to control and modulate the signals. The bracelet 358 may contain a radio-frequency identification (RFID) tag 356. The bracelet 358 may be attached to the patient, and the RFID tag 356 may be programmed with patient-specific identification data (e.g., patient name, birthday, social security number, patient type, stored data regarding prior physiological readings, or other desired data). Alternatively, the RFID tag 356 may be located on a different device, instead of the bracelet 358, that is attached to the patient, such as a necklace, a clip, a pin, or a ring. The RFID tag 356 may be an active tag which transmits to the reader of the RF transceiver 26. Alternatively, the RFID tag 356 may be passive. Generally, RFID tags are passive, such that they are activated and powered by a signal transmitted from the RF transceiver 26, and thus, do not require a battery. Passive RFID tags may reflect or backscatter the signal received from the RF transceiver and add information to the received signal by modulating the reflected or backscattered signal. After the RF transceiver 26 receives the signal from the RFID tag 356, the patient identification data may be decoded by the reader of the RF transceiver 26 and then may be stored by the sensor 10 in the NV memory 86.

The patient monitor 360 of the patient monitoring system 350 may communicate wirelessly with the sensor 10 to receive the physiological parameter signal and the patient identification data. In the illustrated embodiment, the patient monitor 360 is substantially remote from the sensor 10, such that an intermediary wireless receiver 352 may receive the digital detector signal from the sensor 10 and then transmit the signal to the patient monitor 360 for calculation and display on a display 362. However, in other embodiments, the sensor 10 may communicate wirelessly directly with the patient monitor 360.

In other embodiments, it may be desirable to link the patient identification data to the sensor 10 using a scannable barcode. For example, the patient bracelet 358 may include a scannable barcode (not shown) instead of the RFID tag 356. Accordingly, system 350 may be modified to include an optical barcode scanner (not shown), which may be used to link the sensor 10 to the patient. For example, the optical barcode scanner may be communicatively coupled to the patient monitor 360 or the multi-parameter monitor 366. The barcode scanner may be configured to read patient identification data from the scannable barcode located on the patient bracelet 358. Additionally, the sensor 10 may be modified to include a sensor barcode (not shown) relating to identification data for the sensor 10, such as a serial number. As such, the patient monitor 360 and/or the multi-parameter monitor 366 may receive, via the barcode scanner, the identification data from the scannable barcode on the bracelet 358 and from the sensor barcode. The patient monitor 360 and/or the multi-parameter monitor 366 may be configured to link the sets of identification data together in a memory unit of the monitor 360. Accordingly, the sensor 10 may transmit the sensor identification data (e.g., a serial number) along with the digital detector signal so that the patient monitor 360 and/or multi-parameter monitor 366 may identify the detector signal with the correct patient.

Figure 16:
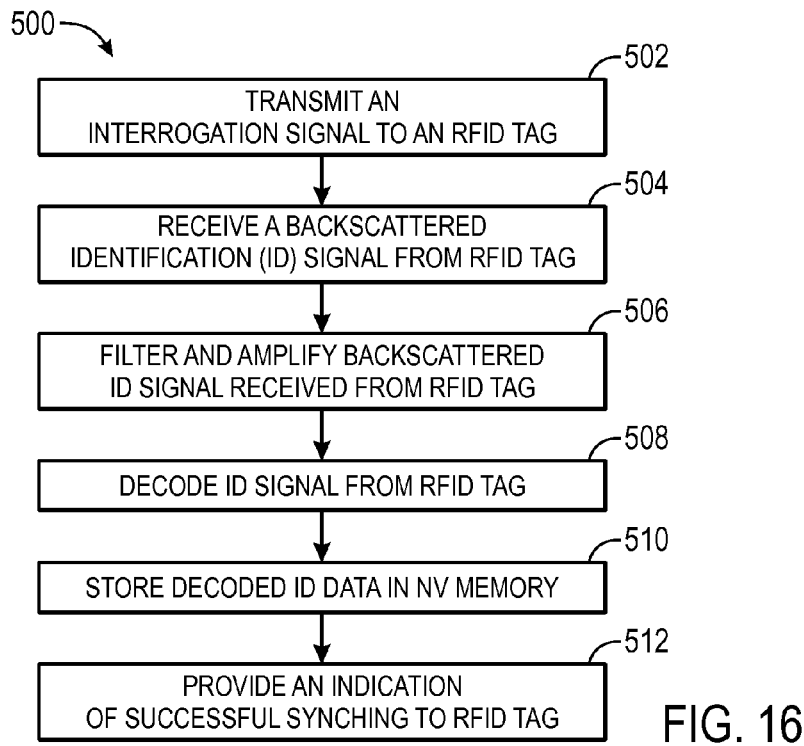
FIG. 16 a flowchart illustrating a process for synching the pulse oximetry sensor of FIGS. 1A-1C with the patient, in accordance with an embodiment.

Accordingly, there are various processes which may be suitable for linking a reusable, wireless sensor to a specific patient. As such, FIG. 16 illustrates a flowchart of an embodiment of a process 500 for linking the sensor 10, which includes the RF transceiver 26, to the RFID tag 356 containing patient identification data on the patient bracelet 358. In the illustrated embodiment, the RFID tag 356 is passive and as such, does not actively and continuously transmit signals to the RF transceiver 26. However, it should be appreciated that the RF transceiver 26 may also operate with an active RFID tag.

To initiate the synching of the sensor 10 to the corresponding patient 382, the sensor 10 transmits an interrogation signal, via the RF transceiver 26, to the RFID tag 356 (block 502). The interrogation signal operates to activate and power the RFID tag 356. In response, the RFID tag 356 may backscatter the interrogation signal and adds identification information by modulating the interrogation signal. As such, the sensor 10 receives a backscattered identification signal, via the RF transceiver 26, from the RFID tag 356 (block 504). The sensor 10 then may filter and amplify the backscattered identification signal (block 506) and decode the signal to retrieve the identification data (block 508). The sensor 10 may store the decoded identification data in the NV memory 86 (block 510). Additionally, the sensor 10 may provide a user-perceivable indication of a successful synching to the RFID tag 356 (block 512). The user-perceivable indication may be an audible indication, such as a beep, a visible indication, such as a light, or a combination of the two.

Figure 17:
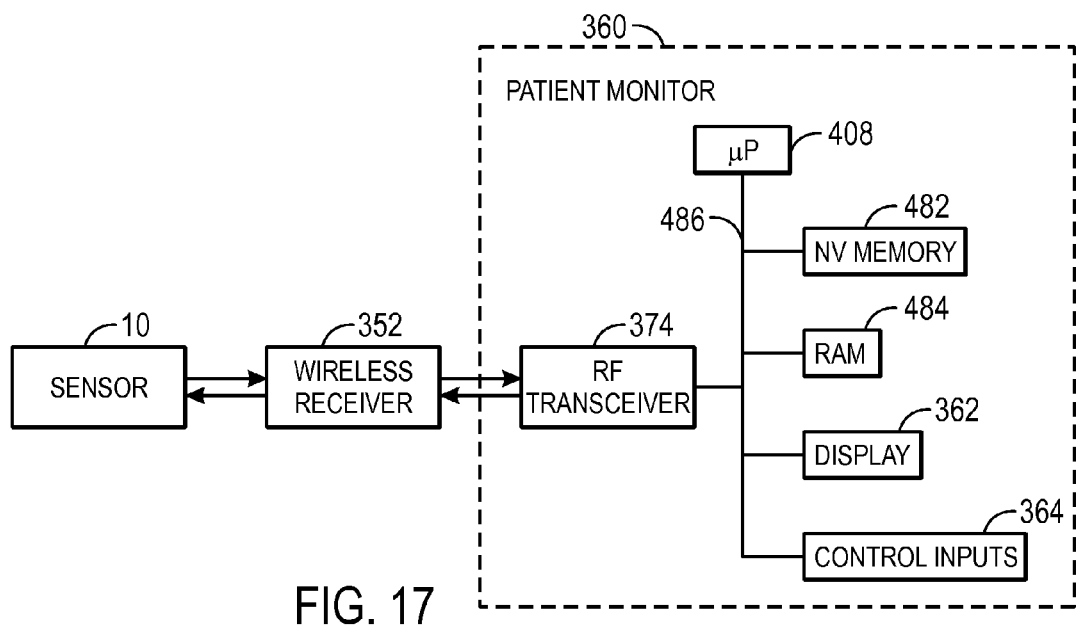
FIG. 17 is a block diagram of the components of an example of the patient monitor of FIG. 15, in accordance with an embodiment.

As described above, the patient monitor 360 may perform the calculation of the physiological parameter and/or receive the patient identification data. Accordingly, FIG. 17 illustrates a block diagram in accordance with an embodiment, which depicts a plurality of components which may be included in the patient monitor 360 to facilitate calculating the physiological parameter and/or linking the sensor 10 to the patient. The patient monitor 360 may include a processor 408, which may be coupled to the main system bus 486 and generally controls the operation of the monitor 360. The processor 408 may execute code such as code for performing diagnostics of the system 350, for measuring and analyzing patient physiological parameters, and so forth. The processor 408 may work in conjunction with NV memory 482 and RAM 484 to determine the physiological parameter of the patient. Furthermore, the processor 408 may store the patient identification data together with the sensor identification data in the NV memory 482, such that the received digital detector signal may be identified to the correct patient. The monitor 360 may also include an RF transceiver 374 coupled to the main bus 486 and controlled by the processor 408. The RF transceiver 374 may facilitate the wireless communication between the monitor 360, the sensor 10, and/or the wireless receiver 352. The patient monitor 360 may be any suitable monitor, such as a pulse oximetry monitor available from Nellcor Puritan Bennett LLC.

In other embodiments, it may be desirable for the sensor 10 to perform the calculation of the physiological parameter instead of the patient monitor 360. As previously described, remote monitoring may be more cost efficient as it may reduce the number of patient monitors 360. Similarly, embodiments in which the sensor 10 includes additional circuitry for the calculation of the physiological parameter may also reduce the number of patient monitors 360 and thus, may be more cost efficient. For example, the sensor 10 may be operable as described above (e.g., to link with the patient) and may additionally transmit a calculated physiological parameter to a display, which may only display the data and not perform any additional processing. To further minimize cost, the sensor 10 may transmit the data to a display that is already available in a patient room and/or an alternative healthcare setting such as a TV monitor.

Figure 18:
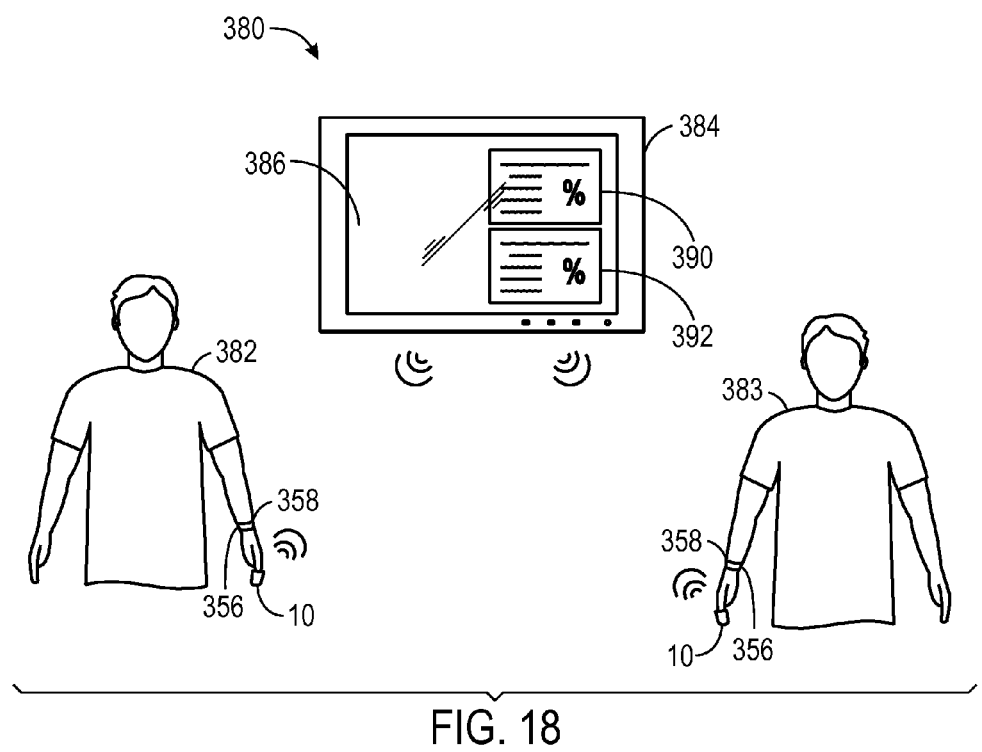
FIG. 18 is a perspective view of a system configured to monitor a physiological parameter of one or more patients, including an embodiment of the pulse oximetry sensor of FIGS. 1A-1C and a TV monitor, in accordance with an embodiment.

With the foregoing in mind, FIG. 18 illustrates a perspective view of a system 380, including the sensors 10, the patient bracelets 358 including the RFID tag 356, and a TV monitor 384. The TV monitor 384 may wirelessly receive signals from the sensors 10, which may include the one or more calculated physiological parameters and corresponding patient identification data relating to patients 382 and 383. The TV monitor 384 may present the data on display 386. In certain embodiments, the data may be sequestered to a region of the display 386 such that the TV monitor 384 may also present standard images (e.g., from a TV show or movie). For example, the patient data may be displayed in regions 390 and 392 such that region 390 may relate to patient 382 and region 392 may relate to patient 383. It should be appreciated that the TV monitor 384 may receive patient data from additional sensors 10.

Figure 19:
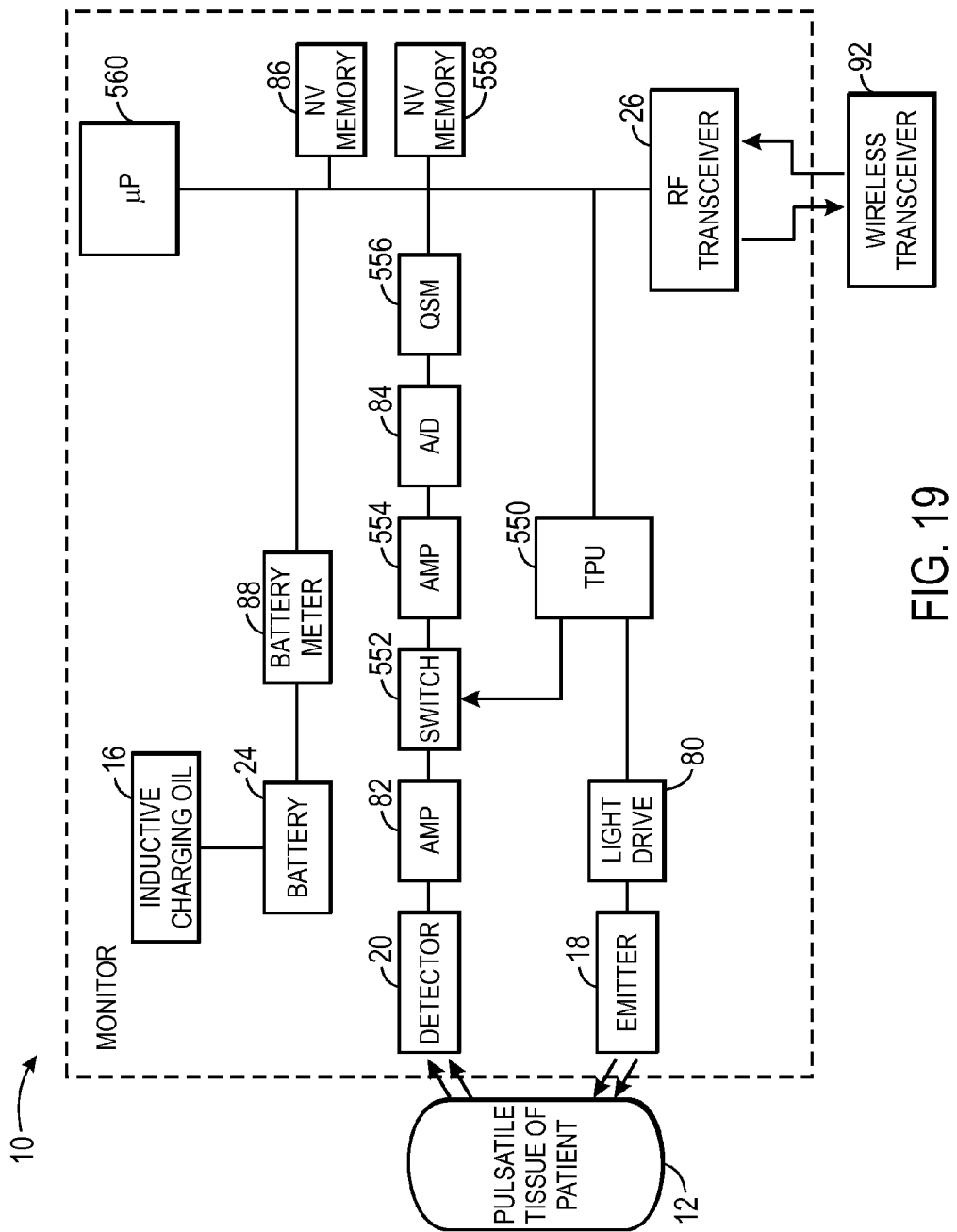
FIG. 19 is a block diagram of the components of an example of the pulse oximetry sensor of FIGS. 1A-1C that may be configured to be used with the system of FIG. 18, in accordance with an embodiment.

To enable the calculation of the physiological parameter, the sensor 10 may include additional or more complex circuitry, as illustrated by the block diagram of FIG. 19. Instead of receiving a wireless signal from the wireless transceiver 92 to drive the light drive 80, as previously described, the sensor 10 may include a time processing unit (TPU) 550 to provide timing and control signals to drive the light drive 80 and control the timing of the emitter 18. The TPU 500 may also control the gating-in of signals from the detector 20 through a switch 552. The sensor 10 may include an additional amplifier 554 and/or a low pass filter (not shown) for additional signal processing before the signal passes through the A/D converter 84. The sensor 10 may also include a queued serial module (QSM) 556 for temporarily storing the digitized detector signal from the A/D converter 84 for later downloading into a random access memory (RAM) 558 as the QSM 556 fills up. The sensor 10 may also include a processor 560 (e.g., an 8-bit or 16-bit microcontroller) to control the operation of the sensor 10.

In an embodiment, the NV memory 86 may include one or more sets of instructions to be executed by the processor 560. For example, based at least in part on the physiological parameter signal provided by the detector 20, the processor 560 may calculate a physiological parameter of interest using various algorithms and coefficient values that may be stored in NV memory 86. These algorithms may include those disclosed in U.S. Pat. No. 4,911,167, filed Mar. 30, 1988, U.S. Pat. No. 6,411,833, filed Nov. 5, 1999, and the Proceedings of the 28$^{th}$ IEEE EMBS Annual International Conference (2006) entitled "INVESTIGATION OF SIGNAL PROCESSING ALGORITHMS FOR AN EMBEDDED MICROCONTROLLER-BASED WEARABLE PULSE OXIMETER," which are all incorporated by reference herein in their entirety for all purposes. For example, in the case of a pulse oximetry sensor 10, NV memory 86 may include algorithms that calculate a $SpO_2$ value using a ratio-of-ratios calculation, in which the $SpO_2$ value is equal to the ratio of the time-variant (AC) and the time-invariant (DC) components of the detector signal acquired using RED light divided by the ratio of the AC and DC components of the detector signal acquired using IR light. In general, a number of processing algorithms may be used to determine the AC and DC components of the detector signal. For example, the DC components of the detector signals may be determined using a number of different methods, including a moving average over a defined time window, an infinite impulse response (IIR) Butterworth low-pass filter, or using a minimum plethysmograph value over a defined time window. Furthermore, for such a calculation, the AC component may be determined using a number of different methods, such as using an average of local plethysmograph derivatives over a period of time, using a derivative-base peak identification and subsequently determining the difference between the amplitude and nadir of each pulse, using a difference in the maximum and minimum values of the plethysmograph waveform over a period of time, and/or using a fast Fourier transform (FFT) with subsequent amplitude analysis. It should be noted that the aforementioned processing algorithms are provided as examples, and number of algorithms may be utilized as would be known to one of ordinary skill in the art.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, individual features of the disclosed embodiments may be combined or exchanged.

What is claimed is:

1. A charging and disinfecting system comprising:
   one or more wireless pulse oximetry sensors configured to generate a physiological signal of a patient, wherein the one or more wireless pulse oximetry sensors comprise a respective inductive coil; and
   a charging and disinfecting device configured to charge and disinfect the one or more wireless pulse oximetry sensors, wherein the charging and disinfecting device comprises:
      a housing having an inlet configured to receive a disinfecting agent;

a wired connection coupled to the housing and configured to receive electrical power from a power supply; and one or more inductive stations disposed in the housing in a vertical arrangement with respect to a base of the housing, wherein each of the one or more inductive stations comprises a pair of prongs vertically extending from a leg coupled to the base of the housing, and wherein at least one prong of the pair of prongs comprises a respective primary inductive coil operable to receive the electrical power from the wired connection, and wherein the pair of prongs is configured to receive and position a respective wireless pulse oximetry sensor of the one or more wireless pulse oximetry sensors within the housing such that the respective primary inductive coil induces an electrical current in each respective inductive coil of the respective one or more wireless pulse oximetry sensors.

2. The system, as set forth in claim 1, wherein the inlet comprises a valve configured to adjust an influx of the disinfecting agent into the housing.

3. The system, as set forth in claim 1, wherein the disinfecting agent is a disinfecting solution.

4. The system, as set forth in claim 1, wherein the disinfecting agent is a disinfecting gas.

5. The system, as set forth in claim 1, wherein the inlet comprises a UV-penetrable region of the housing, and wherein the disinfecting agent is UV light.

6. The system, as set forth in claim 1, wherein the charging and disinfecting device comprises:
a display configured to present status data relating to the one or more wireless pulse oximetry sensors, status data relating to a charging and disinfecting cycle, or a combination thereof; and
a processor configured to send a data transfer signal to each respective wireless pulse oximetry sensor and download the status data from each respective wireless pulse oximetry sensor via inductive data transfer.

7. The system, as set forth in claim 6, wherein the charging and disinfecting device comprises a level sensor adapted to determine an amount of disinfecting agent in the housing and provide an indication of the amount to the processor, a user, or a combination thereof.

8. The system, as set forth in claim 6, wherein the processor is configured to determine a duration of the charging and disinfecting cycle suitable for charging and disinfecting the one or more wireless pulse oximetry sensors based at least in part upon status data relating to the respective wireless pulse oximetry sensor, information regarding the disinfecting agent, or a combination thereof.

9. The system, as set forth in claim 8, wherein each inductive station comprises an indicator configured to be activated by the processor based at least in part upon the data downloaded from respective wireless pulse oximetry sensor.

10. The system, as set forth in claim 6, wherein the processor is configured to control the inlet for receiving the disinfecting agent and to control direction of power from the power supply to the one or more inductive stations, and wherein the processor is configured to control opening of the inlet to enable the entry of the disinfecting agent into the housing and to cause the power supply to direct power to the one or more inductive stations in response to a determination that each respective wireless pulse oximetry sensor is eligible for charging and disinfecting.

11. The system, as set forth in claim 10, wherein the processor is configured to determine that each respective wireless pulse oximetry sensor is eligible for charging and disinfecting by:
downloading a first value from each respective wireless pulse oximetry sensor that is indicative of a number of times the respective wireless pulse oximetry sensor was disinfected;
comparing the first value to a first threshold;
determining that the respective wireless pulse oximetry sensor is eligible for disinfecting in response to a determination that the first value is less than the first threshold;
downloading a second value from each respective wireless pulse oximetry sensor that is indicative of a number of times the respective wireless pulse oximetry sensor was charged;
comparing the second value to a second threshold; and
determining that the respective wireless pulse oximetry sensor is eligible for charging in response to a determination that the second value is less than the second threshold.

12. A charging and disinfecting system comprising:
one or more wireless pulse oximetry sensors configured to generate a physiological signal of a patient, wherein the one or more wireless pulse oximetry sensors comprise a respective inductive coil; and
a charging and disinfecting device configured to charge and disinfect the one or more wireless pulse oximetry sensors, wherein the charging and disinfecting device comprises:
a housing configured to receive a disinfecting agent;
one or more inductive stations disposed in the housing in a vertical arrangement with respect to a base of the housing, wherein each of the one or more inductive stations comprises a pair of prongs vertically extending from a leg coupled to the base of the housing, and wherein at least one prong of the pair of prongs comprises a respective primary inductive coil operable to receive the electrical power from the wired connection, and wherein the pair of prongs is configured to receive and position a respective wireless pulse oximetry sensor of the one or more wireless pulse oximetry sensors within the housing such that the respective primary inductive coil induces an electrical current in each respective inductive coil of the respective one or more wireless pulse oximetry sensors; and
a processor configured to download status data from each respective wireless pulse oximetry sensor and to determine a duration of the charging and disinfecting cycle suitable for charging and disinfecting the one or more wireless pulse oximetry sensors based at least in part upon status data relating to the respective wireless pulse oximetry sensor, information regarding the disinfecting agent, or a combination thereof.

13. The system of claim 12, wherein the processor is configured to control entry of the disinfecting agent into the housing and to cause a power supply to direct power to the one or more inductive stations in response to a determination that each respective wireless pulse oximetry sensor is eligible for charging and disinfecting.

14. The system of claim 13, wherein the processor is configured to determine whether each wireless pulse oximetry sensor is eligible for charging and disinfecting by comparing a first value for each respective wireless pulse oximetry sensor that is indicative of a number of times that the respective wireless pulse oximetry sensor was disinfected to a first threshold for disinfecting and by comparing a second value for each respective wireless pulse oximetry sensor that is indicative of a number of times that the respective wireless pulse oximetry sensor was charged to a second threshold for charging.

15. The system of claim 12, wherein the charging and disinfecting device comprises a display configured to display the status data relating to the one or more wireless pulse oximetry sensors, status data relating to a charging and disinfecting cycle, or a combination thereof.

16. The system, as set forth in claim 1, wherein each pair of prongs is configured to receive and position the respective wireless pulse oximetry sensor of the one or more wireless pulse oximetry sensors such that the respective wireless pulse oximetry sensor is aligned with the respective primary inductive coil.

17. A charging and disinfecting system comprising:
one or more wireless pulse oximetry sensors configured to generate a physiological signal of a patient, wherein the one or more wireless pulse oximetry sensors comprise a respective inductive coil; and
a charging and disinfecting device configured to simultaneously charge and disinfect the one or more wireless pulse oximetry sensors, wherein the charging and disinfecting device comprises:
a housing configured to receive a disinfecting agent; and
one or more inductive stations disposed in the housing in a vertical arrangement with respect to a base of the housing, wherein each of the one or more inductive stations comprises a pair of prongs vertically extending from a leg coupled to the base of the housing, and wherein at least one prong of the pair of prongs comprises a respective primary inductive coil operable to receive the electrical power from the wired connection, and wherein the pair of prongs is configured to receive and position a respective wireless pulse oximetry sensor of the one or more wireless pulse oximetry sensors within the housing such that the respective primary inductive coil induces an electrical current in each respective inductive coil of the respective one or more wireless pulse oximetry sensors.

18. The system, as set forth in claim 17, wherein the charging and disinfecting device comprises a processor, and wherein the processor is configured to determine a duration of the charging and disinfecting cycle suitable for charging and disinfecting the one or more wireless pulse oximetry sensors based at least in part upon status data relating to the respective wireless pulse oximetry sensor, information regarding the disinfecting agent, or a combination thereof.

19. The system, as set forth in claim 18, wherein the processor is configured to control entry of the disinfecting agent into the housing and to cause a power supply to direct power to the one or more inductive stations in response to a determination that each respective wireless pulse oximetry sensor is eligible for charging and disinfecting.

20. The system, as set forth in claim 17, wherein each inductive station comprises an indicator configured to be activated by the processor based at least in part upon data downloaded from the respective wireless pulse oximetry sensor.

21. The system, as set forth in claim 16, wherein the respective primary inductive coil is configured to recharge the respective wireless pulse oximetry sensor without a physical electrical coupling between the respective inductive station and the respective wireless pulse oximetry sensor.

* * * * *